US012311056B2

(12) United States Patent
Lee (10) Patent No.: US 12,311,056 B2
(45) Date of Patent: May 27, 2025

(54) COMPOSITION AND METHOD FOR TREATMENT OF NEUROPSYCHIATRIC DISORDERS (71) Applicant: Duke University, Durham, NC (US)

(72) Inventor: Tong Hyon Lee, Chapel Hill, NC (US)

(73) Assignee: DUKE UNIVERSITY, Durham, NC (US)

(*) Notice: Subject to any disclaimer, the term of this patent is extended or adjusted under 35 U.S.C. 154(b) by 0 days.

(21) Appl. No.: 18/121,626

(22) Filed: Mar. 15, 2023

(65) Prior Publication Data
US 2023/0293443 A1 Sep. 21, 2023

Related U.S. Application Data (63) Continuation of application No. 16/808,458, filed on Mar. 4, 2020, now abandoned, which is a continuation of application No. 15/662,289, filed on Jul. 28, 2017, now abandoned, which is a continuation of application No. PCT/KR2016/000903, filed on Jan. 28, 2016.

(60) Provisional application No. 62/108,616, filed on Jan. 28, 2015.

(51) Int. Cl.
A61K 45/06 (2006.01)
A61K 9/20 (2006.01)
A61K 9/48 (2006.01)
A61K 31/4178 (2006.01)
A61K 31/4458 (2006.01)
A61K 31/48 (2006.01)
A61K 31/517 (2006.01)
A61K 48/00 (2006.01)
A61P 25/22 (2006.01)
A61P 25/30 (2006.01)
A61P 43/00 (2006.01)
A61P 3/04 (2006.01)

(52) U.S. Cl.
CPC .......... A61K 9/48 (2013.01); A61K 9/20 (2013.01); A61K 31/4178 (2013.01); A61K 31/48 (2013.01); A61K 31/517 (2013.01); A61K 45/06 (2013.01); A61K 48/00 (2013.01); A61P 25/30 (2018.01); A61K 31/4458 (2013.01); A61P 3/04 (2018.01); A61P 25/22 (2018.01); A61P 43/00 (2018.01)

(58) Field of Classification Search
CPC ........ A61K 9/48; A61K 9/20; A61K 31/4178; A61K 31/48; A61K 31/517; A61K 45/06; A61K 48/00; A61K 31/4458; A61K 2300/00; A61P 25/30; A61P 3/04; A61P 25/22; A61P 43/00; A61P 1/14; A61P 17/02; A61P 25/00; A61P 25/18; A61P 25/34; A61P 17/14; A61P 25/14; A61P 25/32; A61P 25/36
See application file for complete search history.

(56) References Cited

U.S. PATENT DOCUMENTS

| 6,113,879 | A | 9/2000 | Richards et al. |
| 8,512,751 | B2* | 8/2013 | Rariy .................. A61P 25/00 424/488 |
| 2013/0116215 | A1 | 5/2013 | Coma et al. |

FOREIGN PATENT DOCUMENTS

| WO | WO2003037313 | * | 5/2003 | ........... A61K 31/145 |
| WO | 2007134077 A2 | | 11/2007 | |

OTHER PUBLICATIONS

Davidson et al., Europ. J Pharmacology, 503:99-102, (Year: 2004).*
Robinson et al., Addictive Behaviors, 20(4):481-491, (Year: 1995).*
Preti et al. Addiction Biology, Review: New developments in the pharmacotherapy of cocaine abuse. vol. 12, No. 2, pp. 133-151, Jun. 2007.*
Szabo et al., Translational Development of Novel Pharmacotherapeutic Strategies for Psychostimulant Dependence, Abstract 284, Society of Biological Psychiatry 2010 Annual Meeting (Year: 2010).*
Bhatia, Kamal S., et al. "Reversal of long-term methamphetamine sensitization by combination of pergolide with ondansetron or ketanserin, but not mirtazapine." Behavioural brain research 223.1 (2011): 227-232.
Brensilver et al., "Pharmacotherapy of Cocaine Dependence", Interventions for Addiction, vol. 3, Chapter 46, pp. 439-448.
Clarke, Carl E., et al., "Pergolide versus bromocriptine for levodopa-induced complications in Parkinson's disease." Cochrane Database of Systematic Reviews 2010.1 (1996).
Clinical Trial NCT01377662, published online at on Jun. 21, 2011 Retrieved from: https://clinicaltrials.gov/ct2/show/NCT01377662 Retrieved on: Apr. 30, 2019 (Year: 2011).
Clinicaltrials.gov, NCT01290276, published [online] Feb. 4, 2011 Retrieved from <https://www.clinicaltrials.gov/ct2/show/NCT01290276?term=NCTO 1290276&draw= 1 &rank=1 > Retrieved on Dec. 3, 2019. (Year: 2011).
Grady, Tana A., et al. "Biological and behavioral responses to D-amphetamine, alone and in combination with the serotonin3 receptor antagonist ondansetron, in healthy volunteers." Psychiatry research 64.1 (1996): 1-10.

(Continued)

Primary Examiner — Kimberly Ballard
Assistant Examiner — Stacey N MacFarlane
(74) Attorney, Agent, or Firm — Barnes & Thornburg LLP (57) ABSTRACT The present invention relates to a composition and method for combinative therapy, capable of temporarily regulating inherent dysfunctional neural processes and reducing symptoms and/or signs of neuropsychiatric disorders including, but not limited to, psychostimulant use disorder (PUD) and other substance-related additive disorders, post-traumatic stress disorder (PTSD) and other trauma- and stress-related disorders, and levodopa-induced dyskinesia (LID) and other types of dyskinesias. The present specification shows specific examples of a dosage form.

6 Claims, 2 Drawing Sheets (56) References Cited

OTHER PUBLICATIONS

Kalivas, P. W., and ND3192324 Volkow. "New medications for drug addiction hiding in glutamatergic neuroplasticity." Molecular psychiatry 16.10 (2011): 974-986.

Kampman, https://www.update.com/contents/pharmacotherapy-for-stimulant-use-disorders-in-adults, retrieved on-line Jun. 26, 2019, pp. 1-16.

Koob, George F., and Nora D. Volkow. "Neurocircuitry of addiction." Neuropsychopharmacology 35.1 (2010): 217-238.

Lee, Tong H., et al. "Pharmacologically-mediated reactivation and reconsolidation blockade of the psychostimulant-abuse circuit: a novel treatment strategy." Drug and alcohol dependence 124.1-2 (2012): 11-18.

McLellan, A. Thomas, George E. Woody, and Charles P. O'Brien. "Development of psychiatric illness in drug abusers: Possible role of drug preference." New England Journal of Medicine 301.24 (1979): 1310-1314.

Midha, K. K., et al. "Effects of food on the pharmacokinetics of methylphenidate." Pharmaceutical research 18 (2001): 1185-1189.

Szabo, Steven T et al: "284: Translational Development of Novel Pharmacotherapeutic Strategies for Psychostimulant Dependence", Biological Psychiatry; 65th Annual Convention of the Society-of-Biological-Psychiatry, Elsevier Science, New York, NY; US; New Orleans, LA, USA, vol. 67, No. 9, Suppl. S, May 1, 2010.

Vanover, Kimberly E., et al. "A 5-HT2A receptor inverse agonist, ACP-103, reduces tremor in a rat model and levodopa-induced dyskinesias in a monkey model." Pharmacology Biochemistry and Behavior 90.4 (2008): 540-544.

www.fda.gov/downloads/AdvisoryCommittees/CommitteesMeetingMaterials/Drugs/AdvisoryCommitteeforPharmaceuticalScienceandClinicalPharmacology/UCM207955.pdf published online Apr. 13, 2010 (Year: 2010).

* cited by examiner

COMPOSITION AND METHOD FOR TREATMENT OF NEUROPSYCHIATRIC DISORDERS

CROSS-REFERENCE TO RELATED APPLICATIONS

This application is a continuation of U.S. application Ser. No. 16/808,458, filed Mar. 4, 2020, which is a continuation of U.S. application Ser. No. 15/662,289, filed Jul. 28, 2017, the entire contents of which are hereby incorporated herein in their entirety. U.S. application Ser. No. 15/662,289 is a continuation of International Application No. PCT/KR2016/000903, filed Jan. 28, 2016, and claims benefit of U.S. provisional patent Application No. 62/108,616, filed on Jan. 28, 2015, the disclosures of which are incorporated herein by reference in their entirety for all purposes.

UNITED STATES GOVERNMENT FUNDING AND RIGHTS

The present invention was produced in part using funds from the United States Federal Government under NIH Grant Nos.: R01 DA012768 entitled "Cocaine Withdrawal: A Window of Treatment Opportunity"; R01DA14323 entitled "Medication Development for Methamphetamine Abuse"; NS42124 entitled "Presynaptic Mechanisms and Parkinson's Treatment"; and RC2 DA028905 entitled "Novel Ondansetron Formulation for Combination Treatment of Psychostimulant Abuse." Accordingly, the Federal Government has certain rights to the present invention.

BACKGROUND OF THE INVENTION

1. Field of the Invention

The present invention relates to combination therapy compositions and methods that can temporally modulate underlying dysfunctional neural processes and that can reduce symptoms and/or signs of neuropsychiatric disorders, including, but not limited to, psychostimulant use disorder (PUD) and other substance-related and addictive disorders, post-traumatic stress disorder (PTSD) and other trauma- and stressor-related disorders, and levodopa-induced dyskinesia (LID) and other types of dyskinesia.

2. Description of Related Art

All disorders disclosed herein are classified according to criteria listed in the Diagnostic and Statistical Manual of Mental Disorders Version 5, DSM-5), International Statistical Classification of Diseases and Related Health Problems version 10, ICD-10, or both. In addition, the contents described in the present invention will be readily understood by any person skilled in the art. A number of methods for treatment of neuropsychiatric disorders have been developed, but solutions to their side effects have also been required. Several examples of neuropsychiatric disorders are as follows.

Psychostimulant Use Disorder (PUD)

Misuse of cocaine (COC), methamphetamine (METH) and related drugs (hereinafter collectively referred to as "psychostimulants") continues to impose legal, socioeconomic and medical costs worldwide, not only as a primary psychiatric disorder, but also as a significant comorbid/risk factor in various other neuropsychiatric and medical disorders, e.g., schizophrenia, bipolar disorder, hepatitis C, HIV (See Whiteford et. al., 2013 (Whiteford, H A, Degenhardt, L, Rehm, J, Baxter, A J, Ferrari, A J, Erskine, H E, Charlson, F J, Norman, R E, Flaxman, A D, Johns, N, Burstein, R, Murray, C J L, Vos, T (2013). Global burden of disease attributable to mental and substance use disorders: findings from the Global Burden of Disease Study 2010. The Lancet 382: 1575-1586)).

Despite a high unmet need for effective treatment of psychostimulant use disorder (PUD), more than 20 drugs tested in clinical studies to date have shown only limited efficacy, and no drug is approved by the FDA for this indication. Drugs that are currently used for PUD patients are typically limited to the treatment of comorbid psychiatric conditions. Meanwhile, various psychoactive drugs have been used "off-label" (i.e., without FDA approval) to treat PUD, but the effectiveness thereof has not been strictly tested. Drugs tested in previous clinical trials include other psychostimulants used alone (e.g., d-amphetamine, methylphenidate, etc.), selective dopamine (DA) or serotonin reuptake inhibitors (e.g., fluoxetine), full or partial DA agonists (e.g., aripiprazole), DA antagonists (e.g., risperidone), GABA (γ-aminobutyric acid) agonists (e.g., gabapentin), and CNS stimulant modafinil. While additional drugs (e.g., bupropion, n-acetylcysteine, antiepileptic tiagabine and topiramate, etc.) and other treatment methods (e.g., anti-cocaine and anti-METH vaccines or transcranial magnetic stimulations) continue to be clinically evaluated (see Haile et. al., 2012 (Haile, C N, Mahoney, J J, 3rd, Newton, T F, De La Garza, R, 2nd (2012). Pharmacotherapeutics directed at deficiencies associated with cocaine dependence: focus on dopamine, norepinephrine and glutamate. Pharmacol Ther 134: 260-277)), but the common pattern of treatment results in such clinical trials is that: (1) treatments showing potential in small-scale clinical trials does not demonstrate efficacy in larger trials (for example, Vigabatrin); or (2) they show efficacy only in patients of specific subgroups (for example, modafinil and topiramate were effective only in patients without alcohol use disorders, and disulfiram was effective in only ⅓ of patients with specific genotypes and patients who received anti-cocaine vaccines inducing specific antibody responses). Thus, there remains an urgent, unmet need for a consistently effective medication for psychostimulant use disorder with objective neurobiological endpoint measures that reflect reductions in illicit use of psychostimulants.

Unlike sub-optimal therapeutic outcomes in human clinical trials or medical practices, selected combinations of DA agonists and 5HT2, 5-HT3 or NK-1 receptor antagonists can reverse behavioral and neurobiological changes observed in sensitization and self-administration animal models of PUD. Thus, as reviewed in recent literature (see Lee et al., 2012 (Lee, T H, Szabo, S T, Fowler, J C, Mannelli, P, Mangum, O B, Beyer, W F, Patkar, A, Wetsel, W C (2012). Pharmacologically-mediated reactivation and reconsolidation blockade of the psychostimulant-abuse circuit: a novel treatment strategy. Drug and alcohol dependence 124: 11-18), these treatments: (1) reverse previously established COC or METH behavioral sensitization; (2) attenuate self-administration under progressive ratio and drug-induced reinstatement paradigms; and (3) normalize associated neurobiological marker changes. Important findings from these investigations include: (1) consistent treatment efficacy in animal models is achieved if and only if the antagonist is given 3.5 hours after, but not before or with, the agonist; and (2) daily DA agonists or 5-HT antagonists given alone are ineffective.

While the combination therapy method, whereby a 5HT2, 5-HT3 or NK-1 receptor antagonist is administered to animals after the fixed delay of 3.5 hrs. after administration of a DA agonist, was well established in animal models of PUD (see Lee et al., 2012 supra), the utility of these treatments in humans were limited by their strict dependence on the obligatory dosing regimen (i.e., agonist followed 3.5 h later by antagonist) that forces patients to administer the two drugs at the respective prescribed time points in order to obtain any therapeutic benefits. This lack of practical means to ensure treatment compliance is especially problematic for PUD and other psychiatric patients, who, because of their primary or comorbid psychiatric diagnoses, are typically unwilling or unable to adhere to prescribed treatment plans. Thus, successful use of the combination therapy in these patients is typically limited to monitored settings such as inpatient or residential treatment facilities, and attempts to treat PUD patients in an outpatient setting will lead to failure to meet the treatment objective of reduced illicit drug use.

Levodopa-Induced Dyskinesia

In patients diagnosed with Parkinson's disease and/or other related disorders (hereinafter correctively abbreviated as "PD"), DA replacement treatments are used to alleviate symptoms and signs of PD and other related disorders by restoring DA signaling in the brain. The dopamine (DA) precursor levodopa (L-3,4-dihydroxyphenylalanine) is one of the most effective drugs for alleviating PD symptoms and signs in PD patients. However, its propensity to induce levodopa-induced dyskinesia (LID) and associated efficacy loss continue to limit its usefulness in the long-term management of PD patients. Even with "optimal" therapeutic management, up to 90% of PD patients develop LID over 5 to 10 years. LID is one of the main reasons for the failure of levodopa treatment (with or without adjunctive dopamine agonists) of PD patients.

Levodopa Sensitization

Among various mechanisms, levodopa sensitization plays an important role in the development and maintenance of LID. Dysregulation of DA synthesis, release and clearance of extracellular DA (due to progressive DA neuronal death and/or "ectopic" DA synthesis and release by 5-HT terminals) is thought to lead to exaggerated fluctuations in the synaptic DA concentrations following levodopa administration. These fluctuations, in turn, induce dysfunctional synaptic alterations in the basal ganglia and other brain areas.

Based on the putative role of fluctuating synaptic DA levels, various strategies designed to maintain sustained levodopa levels have been utilized to block LID (sensitization) development or to counteract levodopa sensitization expression via induction of tolerance. Such strategies include: (1) use of controlled- or extended release levodopa formulations or "round-the-clock" levodopa dosing regimen; (2) addition of a catechol-O-methyltransferase inhibitor to reduce synaptic DA concentration fluctuations; (3) intra-duodenal levodopa infusion; and (4) use of levodopa patches. Unfortunately, these "sustained" levodopa approaches have not been as effective as originally expected. Potential reasons for this less-than-optimal efficacy may include but not limited to: (1) reduced peak levodopa concentrations (for a given "equivalent" dose); (2) development of pharmacodynamic tolerance; and (3) emergence of new, distinct neurobiological alterations during prolonged "continuous" levodopa treatment, a well-documented phenomenon for direct and indirect DA agonists. It is also noted that maintaining the levels of a DA agonist for up to 12-14 hours/day still leads to behavioral sensitization, whereas more extended sustainment of drug concentrations (e.g., greater than 18 hours/day infusion) is required for tolerance induction (see Ellinwood et al., 2002 (Ellinwood, E H, Davidson, C, Yu, G Z, King, G R, Lee, T H (2002). Effect of daily dosing duration of direct and indirect dopamine receptor agonists: cocaine cross-tolerance following chronic regimens. European neuropsychopharmacology 12: 407-415)). Maintenance of drug concentrations within the effective therapeutic range for extended periods of time is expected to frequently lead to increased incidences of nighttime side effects such as nightmares, sleep disturbances, etc. These considerations suggest that numerous factors, including individual differences in drug metabolism, ability to adhere to prescribed dosing regimen, and/or therapy non-compliance due to increasing LID or other side effects may potentially lead to variability in the duration of the sustained levodopa levels—thus limiting the utility of "sustained" treatments as an "anti-LID" strategy.

In addition to "sustained" levodopa therapies, other "anti-LID" strategies include substitution of levodopa with an alternative drug or concomitant administration of an "anti-LID drug" with levodopa to prevent LID development or block expression of preexisting LID. In addition, many treatment candidates at various stages of development are being evaluated. Recently, deep brain stimulation (DBS) has been also increasingly utilized, although, in addition to its invasive nature and risks for short- and long-term postoperative complications, it is yet to be systematically determined whether this procedure directly modifies critical neurobiological alterations underlying LID or only indirectly does so by allowing for reduced levodopa doses, secondary LID expression blockade and/or slowing down PD progression.

Post-Traumatic Stress Disorder (PTSD)

The US National Comorbidity Survey Replication (NCS-R) estimated the 12-month prevalence of PTSD among adult Americans to be 3.5%. Of these cases, 36.6% are considered to be severe based on the symptoms. The overall lifetime prevalence of PTSD in the USA is estimated to be 8 to 9%, costing about $8 billion, and is twice as common in women as in men. The 12-month prevalence was found to be 1.8% among men and 5.2% among women (National Institute of Mental Health, 2010). In adolescents (aged 13-18 years old) this prevalence is about 4%. As a result of such high prevalence, a large number of people are being treated every year with a 12-month treatment seeking rate of 49.9% in the USA, with about 42% of these patients receiving minimally adequate treatment.

In South Korea, the Korean National Health Insurance statistical data indicate that the total number of PTSD patients (outpatients and inpatients) was 6,981 in 2014, 6,741 in 2013, and 6,950 in 2012. When analyzing the number of total patients by gender, the number of male patients was 1.5 times higher than that of female patients. Within a range from 10- to 60-years old, the number of patients was evenly distributed across all ages.

Current treatment options listed as having "significant" or "some" benefit in the "Post-Traumatic Stress Disorder Pocket Guide", 2013 (Pocket Guide) include both psychotherapies (e.g., "cognitive", "exposure" therapies) and pharmacotherapies. With respect to pharmacotherapies, monotherapies with antidepressants, especially selective serotonin or serotonin/norepinephrine reuptake inhibitors, have shown efficacy in randomized controlled trials; with only sertraline and paroxetine being approved by the Food and Drug Administration (FDA) for the treatment of PTSD. Although benzodiazepines, atypical antipsychotics, anticonvulsants have been also examined, these agents have not shown consistent efficacy, and are not currently on the recommended drug list in the aforementioned guideline. Combination of exposure therapy and paroxetine has been reported to produce no additional therapeutic efficacy compared to exposure therapy only. Additional treatments and investigational new drugs (IND) continue to undergo clinical trial evaluations as either monotherapies or as augmentation strategies to existing forms of PTSD treatment.

Neural Basis of Neuropsychiatric Disorders

Various neuropsychiatric disorders, including PUD, LID and PTSD, may be regarded as a consolidated form of maladaptive dysfunctional neural circuit (dysfunctional neural plasticity). Disorder-specific neural plasticity changes at various levels, including but not limited to the levels of neural mechanisms and processes, brain areas, brain area connectivity, brain networks and network interactions within and without the brain, are considered to underlie the signs and symptoms of specific disorders (see Headley and Pare, 2013 (Headley, D B, Pare, D (2013). In sync: gamma oscillations and emotional memory. Front Behav Neurosci 7: 170)). Thus, treatment-mediated normalization of such changes in neural plasticity might result in successful therapeutic results.

Figure 1:
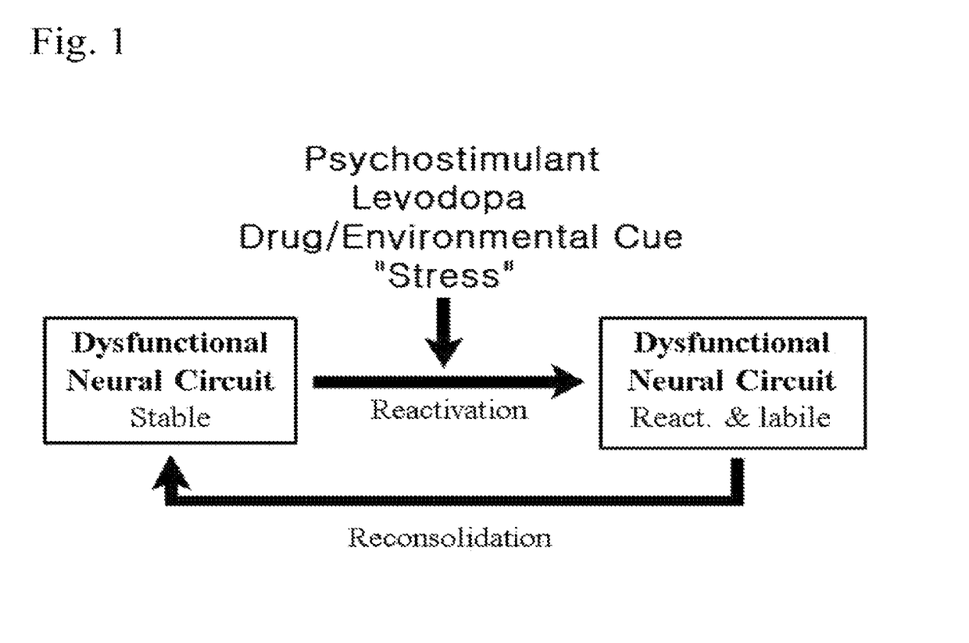
FIG. 1 schematically illustrates the neural processes underlying the maintenance of a dysfunctional neural circuit.

FIG. 1 schematically illustrates the neural processes underlying the maintenance of a dysfunctional neural circuit.

In patients diagnosed with PUD, the stable, consolidated "PUD neural circuit" may be reactivated by exposure to various stimuli such as psychostimulants themselves (for example, "drug tasting"), environmental cues associated with drug use (e.g., seeing drug paraphernalia) or "stress" (see Childress et al., 1999 (Childress, A R, Mozley, P D, Mcelgin, W, Fitzgerald, J, Reivich, M, O'brien, C P (1999). Limbic activation during cue-induced cocaine craving. The American journal of psychiatry 156: 11-18); Sinha, 2006 (Sinha, R, Garcia, M, Paliwal, P, Kreek, M J, Rounsaville, B J (2006). Stress-induced cocaine craving and hypothalamic-pituitary-adrenal responses are predictive of cocaine relapse outcomes. Archives of general psychiatry 63: 324-331); Lee et al., 2012 supra). Unless interfered with, reactivated memory becomes reconsolidated during withdrawal (e.g., "crash").

LID is another consolidated form of dysfunctional neural plasticity changes ("LID neural circuit"), which is maintained by repeated reactivation following therapeutic levodopa administration and subsequent reconsolidation during pharmacokinetic (PK) and/or pharmacodynamic (PD) decline of therapeutic effects of levodopa.

Similar to the dysfunctional PUD or LID neural circuits, the dysfunctional "PTSD neural circuit" in PTSD patients may be conceptualized as being maintained through repeated reactivation and reconsolidation cycles. For example, the dysfunctional neural circuit may be reactivated when a patient is exposed to stimuli that were previously associated with the causative traumatic stressful event (e.g., any loud noise that reminds the patient of a bomb explosion that killed a friend, getting inside a car after being in a major auto accident, etc.). This reactivation leads to reemergence of PTSD symptoms and signs, and symptoms and signs subsides when the reactivated PTSD circuit reconsolidates into the stable but readily-reactivatable state. Upon the reconsolidation, PTSD symptoms and signs abates, ready to reemerge upon the next encounter with stimuli.

BRIEF SUMMARY OF THE INVENTION

It is an object of the present invention to provide combination therapy compositions and methods, which may, by temporally modulating the underlying dysfunctional neural processes, reduce symptoms and/or signs of neuropsychiatric disorders, including, but not limited to, psychostimulant use disorder (PUD) and other substance-related and addictive disorders, post-traumatic stress disorder (PTSD) and other trauma- and stressor-related disorders, and levodopa-induced dyskinesia (LID) and other types of dyskinesia.

Based on the conceptualization presented above, the present invention provides combination compositions and methods comprised of two active ingredients. One of the ingredients, a DA agonist, is first delivered to reactivate the consolidated, stable dysfunctional neural circuit to its "reactivated and labile" state. The second ingredient, a 5-HT2, 5-HT3 or NK-1 antagonist, is delivered at a suitable time after the first ingredient to block reconsolidation and subsequent memory restabilization. Thus, the invention is designed to sequentially reactivate the dysfunctional neural circuit and to block its reconsolidation, resulting in progressive reduction in the symptoms and/or signs of neuropsychiatric disorders to subclinical levels. Disorders that can be treated with the combination therapy include but not limited to psychostimulant use disorder (PUD) and other substance-related and addictive disorders, post-traumatic stress disorder (PTSD) and other trauma- and stressor-related disorders, and levodopa-induced dyskinesia (LID) and other types of dyskinesia.

The present invention provides combination therapy compositions and methods, which may, by temporally modulating the underlying dysfunctional neural processes, reduce symptoms and/or signs of neuropsychiatric disorders, including, but not limited to, psychostimulant use disorder (PUD) and other substance-related and addictive disorders, post-traumatic stress disorder (PTSD) and other trauma- and stressor-related disorders, and levodopa-induced dyskinesia (LID) and other types of dyskinesia. Furthermore, the compositions and the methods embodied in the present disclosures may be effective in the treatment of: (1) other substance-related disorders, including but not limited to tobacco use disorder, alcohol use disorder and cannabis use disorder; (2) behavioral addictive disorders, including but not limited to compulsive gambling and internet addictions; (3) other trauma and stressor-related disorders, including but not limited to reactive attachment disorder, acute stress disorder and adjustment disorder; (4) anxiety disorders, including but not limited to generalized anxiety disorder, panic disorder, agoraphobia and substance/drug-induced anxiety disorders; (5) obsessive-compulsive disorders, including but not limited to body dysmorphic disorder, hoarding disorder, trichotillomania, and excoriation disorder; and (6) eating disorders, including but not limited to, anorexia nervosa, bulimia nervosa, and binge-eating disorder.

DETAILED DESCRIPTION OF THE INVENTION

Hereinafter, detailed description of one or more embodiments of the present invention will be provided in combination with the drawings which explain the principles of the present invention. The present invention is described in combination with these embodiments, but is not limited to any embodiment. The scope of the present invention covers many alternative solutions, modifications and equivalents, and is only limited by the claims.

Those skilled in the art can easily understand that the present invention can be well adapted to attain the objectives and advantages mentioned as well as those which are inherent therein. The detained description described herein represents currently preferred embodiments, is illustrative only, and is not intended to limit the scope of the present invention. Those skilled in the art will envision other modifications and uses within the scope and spirit of the present invention as defined by the claims.

Many specific details are set forth in the following description to provide a thorough understanding of the present invention. These details are provided for the purpose of examples, and the present invention can be practiced according to the claims in the case of lacking some or all of these specific details. For clarity, the technical materials known in the technical field related to the present invention have not yet been described in detail, to avoid unnecessarily obscuring the present invention.

All disorders disclosed herein are classified according to criteria listed in the Diagnostic and Statistical Manual of Mental Disorders Version 5, DSM-5), International Statistical Classification of Diseases and Related Health Problems version 10, ICD-10, or both. Target indications described in the present invention may include primary disorders, secondary disorders, side effects, or comorbid conditions.

As described in "Background Art" section, various neuropsychiatric disorders, including but not limited to PUD, LID and PTSD, can be conceptualized as stable, consolidated forms of dysfunctional, maladaptive synaptic plasticity, which are maintained by repeated reactivation/reconsolidation cycles. While limited pharmacological options are currently available for various neuropsychiatric disorders, most of these treatments may be considered to be only "palliative" to the extent that they are mainly used to mitigate signs and symptoms of the targeted primary and/or comorbid disorders. There is an unmet medical need for more effective pharmacological treatment that can normalize the underlying dysfunction neural circuit ("disease modification").

Figure 2:
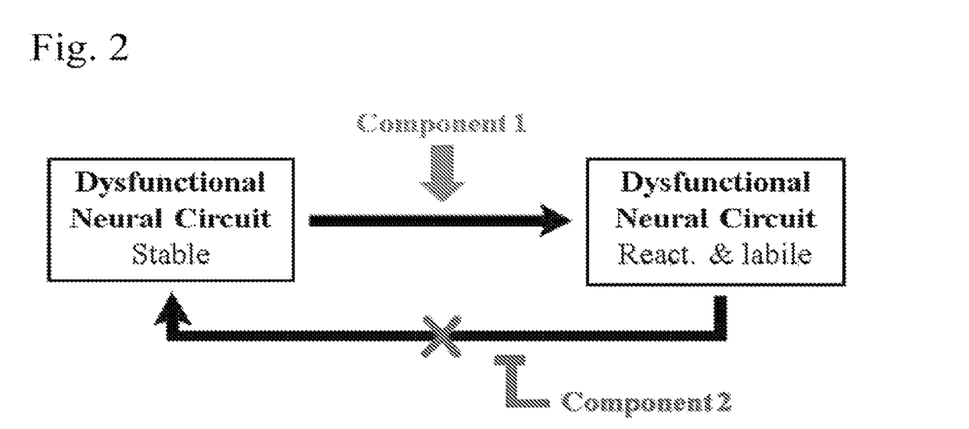
FIG. 2 shows a conceptual model of combination therapy embodied in the present invention.

FIG. 2 shows a conceptual model of combination therapy embodied in the present invention.

The combination therapy is comprised of two active ingredients (Component 1 and Component 2, FIG. 2). Component 1 (FIG. 1) therapeutically reactivates the maladaptive memory underlying NS Disorder from Stable State to Transition State, thereby rendering it transiently labile. Component 2 incorporated as a therapeutic method, composition, formulation or dosage form into the same embodiment as Component 1 blocks the reconsolidation and subsequent restabilization of the maladaptive memory back to Stable State. Thus, the therapeutic embodiments described herein allow for delivery of the combination therapy in optimized and convenient formats and manners, leading to progressive reduction of signs and symptoms of targeted disorders to subclinical levels. The compositions, methods and examples promote patient compliance, and enable the combination therapy to be effectively applied as a single dosage form therapy in clinical practices.

The combination therapy, comprised of two active ingredients and described herein, may be used for treatment of neuropsychiatric disorders. Disorders that may be treated by the combination therapy include PUD, LID and PTSD. Additional disorders include but not limited to: (1) other substance-related disorders, including but not limited to tobacco use disorder, alcohol use disorder and cannabis use disorder; (2) behavioral addictive disorders, including but not limited to compulsive gambling and internet addictions; (3) other trauma and stressor-related disorders, including but not limited to reactive attachment disorder, acute stress disorder and adjustment disorder; (4) anxiety disorders, including but not limited to generalized anxiety disorder, panic disorder, agoraphobia and substance/drug-induced anxiety disorders; (5) obsessive-compulsive disorders, including but not limited to body dysmorphic disorder, hoarding disorder, trichotillomania, and excoriation disorder; and (6) feeding and eating disorders, including but not limited to anorexia nervosa, bulimia nervosa, and binge-eating disorder.

While differential symptoms, signs, specific brain circuits and other diagnostic criteria distinguish the above neuropsychiatric disorders, they share the common property of being forms of consolidated dysfunctional neural plasticity. Furthermore, these disorders share one or more identical neurotransmitters, receptors, molecules or signaling pathways, such as dopamine, glutamate, brain-derived neurotrophic factor ((BDNF), dopamine receptor subtypes, α-amino-3-hydroxy-5-methyl-4-isoxazolepropionate (AMPA), N-methyl-D-aspartate (NMDA) and metabotropic glutamate 5 (mGluR5) receptors and various protein kinases and pseudokinases in the formation, consolidation and/or maintenance of individual dysfunctional neural circuits. Thus, these diseases may be amenable to therapeutic intervention by the combination therapy described herein.

The combination therapy may be administered in any compositions, dosage forms, methods or administration routes compatible with clinical practices, which are understood and executed in the field to which the present invention pertains. Component 1 reactivates the maladaptive dysfunctional neural circuit from a stable state to a reactivated and transiently labile state. Component 2 incorporated into the same composition, formulation or dosage form as Component 1 blocks reconsolidation and subsequent restabilization of the reactivated neural circuit to a stable state. Thus, the single composition, formulation or dosage form optimizes the combination therapy, and allows the two active ingredients to be delivered in vivo in such a manner to ensure high patient compliance, thereby reducing symptoms and signs of the target disorder to subclinical levels. The compositions, formulations, methods and exemplary embodiments described herein enable the combination therapy to be effectively applied as a single dosage form.

1. Component 1 may be selected from small molecules, other types of molecules, and modifications thereof (for example, formulations, prodrugs, etc.). The other types of molecules include, but are not limited to, small interfering ribonucleic acids (siRNAs), micro-RNAs, antisense oligonucleotides, aptamers, peptides, proteins (e.g., antibodies), naturally occurring organic or inorganic molecules, chemical elements (e.g., lithium), and any synthetic compounds greater or smaller than small molecules. Component 1 may be included in a single composition, formulation and dosage form, together with Component 2, which may be delivered by any safe, acceptable and effective dosing method to reactivate the dysfunctional neural circuit from a stable state to a reactivated and labile state.

2. In one embodiment of the combination therapy, component 1 is a pharmacologically effective indirect or direct DA agonist or a pharmaceutically acceptable salt thereof, with or without norepinephrine (NE) and/or serotonin (5-HT) agonistic efficacy. If a direct DA agonist is selected as Component 1, this agonist may or may not show a preference for the D1-like or the D2-like DA receptor. Importantly, unless otherwise specified, the terms "D1" and "D1-type" are used interchangeably with each other to denote either or both of the D1 and D5 receptors. Similarly, the term "D2" and "D2-type" are used interchangeably with each other to denote each of the D2, D3 and D4 DA receptors or any combinations thereof. If stereoisomers of the substance selected as Component 1 exist, any stereoisomers may be used alone or in a combination in optimized proportions. Component 1 may be also the substances described in Section 1 or modifications thereof, which are or are expected to be functional DA agonists based on: (1) their physiochemical characteristics, as evaluated by any analysis methods known to those skilled in the art, including but not limited to pharmacophore-based "docking", virtual computational screening and other in vitro/in silico analysis methods; and/or (2) their in vitro and/or in vivo pharmacological profiles.

2.1. Where an indirect DA agonist (e.g., DA precursor, DA releasing agent or a DA reuptake blocker) is selected as Component 1, an agonist that also acts as a pharmacologically effective NE and/or 5-HT agonist (e.g., d-amphetamine, methylphenidate, or a selective dopamine/norepinephrine reuptake inhibitor) is preferable to a DA agonist that is not a pharmacologically effective NE and/or 5-HT agonist (e.g., a selective DA reuptake blocker).

2.2. Where a direct DA agonist is selected as Component 1, a non-selective D1-type or D2-type DA receptor agonist is preferable to a D1-selective or D2-selective receptor agonist.

2.3. Where a direct DA agonist is selected as Component 1, an agonist that also acts as a pharmacologically effective NE and/or 5-HT agonist is preferable to those showing no NE and/or 5-HT efficacy.

2.4. Agonists and pharmaceutically-acceptable salts and any modified forms thereof, which exhibit immediate and pulsatile release profiles in any in vitro or in vivo tests that are well-known to those skilled in the art (e.g., in vitro dissolution test, direct determination of pharmacokinetic parameters in humans), are preferable to any other combinations/permutations of immediate, delayed, pulsatile, and extended/sustained-release profiles. One preferred in vitro release profile of an agonist is a dissolution rate of greater than or equal to 90% in less than or equal to 2 hours under simulated gastric or intestinal dissolution test conditions, and even more preferred profile is a dissolution rate of greater than or equal to 80% dissolution in less than or equal to 1 hour under identical test conditions.

2.5. Agonists and pharmaceutically acceptable salts and modifications thereof (including any one or all of active metabolites) may have a terminal elimination half life (t½) of 20 hours or less in the human body. A preferred terminal elimination half life (t½) is 10 hours or less, and an even more preferred terminal elimination half life (t½) is 5 hours or less.

3. Component 2 may be selected from small molecules, other types of molecules, and modifications thereof (for example, formulations, prodrugs, etc.). Other types of molecules include, but are not limited to, small interfering ribonucleic acids, micro-RNAs, antisense oligonucleotides, aptamers, peptides, proteins (e.g., antibodies), naturally occurring organic or inorganic molecules, chemical elements (e.g., lithium), and any synthetic compounds greater or smaller than small molecules. Component 2 may be incorporated into single dosage forms with Component 1 for combination therapy, which may be delivered by any safe, acceptable and effective route of administration, to block reconsolidation of dysfunctional neural circuit after Component 1 reactivates it to a labile state from its stable state.

4. In one embodiment, Component 2 is selected from selective or non-selective receptor antagonists or inverse-agonists of the 5-HT2 receptors, selective or non-selective receptor antagonists or inverse-agonists of the 5-HT3 receptor, or selective or non-selective receptor antagonists or inverse-agonists of the NK-1 receptor, inclusive of all 5-HT2, 5-HT3 and NK-1 receptor subtypes, single nucleotide polymorphisms and other transcriptional, translational and post-transcriptional modifications of respective receptors expressed in humans. Specific examples include, but are not limited to, ketanserin and its chemical homologues (e.g., mianserin); mirtazapine and its chemical homologue (e.g., setiptiline); ondansetron, granisetron, dolasetron, palonosetron and tropisetron.

If stereoisomers of the substance selected as Component 2 exist, any stereoisomers may be used alone or in combination in optimized proportions.

Component 2 may be also the substances described in Section 3 or modifications thereof, which are or are expected to be functional antagonists at the 5-HT3, 5-HT2 and/or NK-1 receptors based on: (1) their physiochemical characteristics, as evaluated by any analysis methods known to those skilled in the art, including but not limited to pharmacophore-based "docking", virtual computational screening and other in vitro/in silico analysis methods; and/or (2) their in vitro and/or in vivo pharmacological profiles.

4.1. Where a 5-HT2 antagonist or an inverse-agonist is selected as component 2, an antagonist or an inverse-agonist selective for the 5-HT2A subtype, 5-HT2C subtype or both of the 5-HT2A and 5-HT2C subtypes is preferable to other antagonists or inverse-agonists selective for other 5-HT2 subtypes.

4.2. Where a 5-HT3 antagonist or an inverse-agonist is selected as component 2, the antagonist or inverse-agonist may or may not show biochemical, in vitro and in vivo pharmacological properties or profiles, which are predictive of the substance being an antagonist, an inverse-agonist or a full or partial agonist at the α7 nicotinic receptor. A selective 5-HT3 antagonist is preferred over a 5-HT3 antagonists that is or is predicted to be a pharmacologically-effective α7 nicotinic antagonist, an inverse agonist or a full or partial agonist.

4.3. Where a pharmacologically effective NK-1 antagonist or inverse-agonist is selected as component 2, the antagonist or inverse-agonist may or may not be selective for the NK-1 receptor subtype compared to the NK-2 and/or NK-3 receptor subtypes. A non-selective NK-1 antagonist is preferable to a selective NK-1 antagonist.

4.4. Antagonists and pharmaceutically-acceptable salts and any modified forms thereof, which exhibit a delayed and pulsatile release profile in any in vitro or in vivo tests that are well-known to those skilled in the art (e.g., in vitro dissolution test, direct determination of pharmacokinetic parameters in humans), are preferred over those with any other combinations/permutations of immediate, delayed, pulsatile, extended and sustained release profiles. One preferred in vitro release profile of an antagonist is a dissolution rate of less than or equal to 10% in greater than or equal to 3 hours and a rate greater than or equal to 80% in less than or equal to 7 hours in simulated gastric or intestinal fluid.

4.5. Antagonists and pharmaceutically acceptable salts and modifications thereof (including any one or all of active metabolites) may have a terminal elimination half-life (t½) of 20 hours or less in the human body. A preferred terminal elimination half-life (t½) is 16 hours or less, and a more preferred terminal elimination half life (t½) is 14 hours or less. Even more preferred terminal elimination half life (t½) is 3 to 13 hours.

5. The maximum concentration of any drug following an in vivo administration is termed "Cmax," and the time at which the Cmax is reached is termed "Tmax." The difference between the Tmax of a pharmacologically active form of component 1 and the Tmax of a pharmacologically active form of component 2 plays an essential role in determining the efficacy of combination therapy. For all therapeutic indices described herein, the Tmax separation between the plasma or serum concentration of a pharmacologically active form of component 1 and that of a pharmacologically active form of component 2 in humans may range from 1 hour to 12 hours. A preferred Tmax separation is 1 to 8 hours, more preferably 2 to 8 hours, and even more preferably 2 to 7 hours.

6. Tmax of Component 1 and/or Component 2 may be modified through various methods including but not limited to: (1) the use of a pharmacologically-inactive prodrug that undergoes activation in, including but not limited to, the gastrointestinal track, blood, liver or other organs; or (2) formulation-based modification of the pharmacologically-effective parent form. Various formulation-based methods including but not limited to pH-based, osmotic-based, liposome-based modification methods may be used to achieve the intended in vivo PK profiles in humans.

7. Compositions for combination therapy may be provided as any dosage forms, including, but not limited to, tables, capsules, gels, suspensions, films, patches and suppositories. The dosage forms may be pharmaceutical compositions containing component 1 and component 2 as active ingredients and may further contain pharmaceutically acceptable additives for formulation, such as excipients, carriers or the like. The additives may be any pharmaceutically acceptable additives that may assist in formulation such as molding and facilitate intake. For examples, the compositions may contain a predetermined amount of the active ingredients in powder or granules, a solution or a suspension in an aqueous or non-aqueous liquid, an oil-in-water or water-in-oil emulsion. Such formulations may be prepared by any suitable method of pharmacy which includes the step of bringing into association the active compound and a suitable carrier which contains one or more accessory ingredients. In general, the compositions are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the active ingredient in a free-flowing form, such as a powder or granules optionally mixed with an excipient, such as a binder, lubricant, inert diluent, and/or surface active agent. Molded tablets may be made by molding, in a suitable machine, the powdered compound moistened with an inert liquid binder.

The present invention further encompasses anhydrous pharmaceutical compositions and dosage forms containing the active ingredient, since water can facilitate the degradation of some compounds. For example, the addition of water is widely accepted in the pharmaceutical field as a means of simulating long-term storage in order to determine characteristics such as shelf-life or the stability of formulations over time. Anhydrous pharmaceutical compositions and dosage forms of the present invention can be prepared using anhydrous or low moisture containing ingredients and low moisture or low humidity conditions. Pharmaceutical compositions and dosage forms of the present invention, which contain lactose, are preferably anhydrous if substantial contact with moisture and/or humidity-during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

The active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, preferably without employing the use of lactose. For example, suitable carriers include powders, capsules, and tablets, with the solid oral preparations being preferred. If desired, tablets can be coated by standard aqueous or non-aqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants are used in the compositions of the present invention to provide tablets that disintegrate when exposed to an aqueous environment. An excessively large amount of a disintegrant will produce tablets which may disintegrate in the bottle. An excessively small amount of a disintegrant may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compound disclosed herein. The amount of disintegrant used may vary based upon the type of formulation and mode of administration, and is readily discernible to those of ordinary skill in the art. Typically, about 0.5 to about 15 wt % of disintegrant, preferably about 1 to about 5 wt % of disintegrant, may be used in the pharmaceutical composition.

Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, or mixtures thereof.

Lubricants which can be used to form the pharmaceutical compositions and dosage forms of the present invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof.

Additional lubricants include, for example, a syloid silica gel, a coagulated aerosol of synthetic silica, or mixtures thereof. A lubricant may optionally be added in an amount of less than about 1 wt % of the pharmaceutical composition.

When aqueous suspensions and/or elixirs are desired for oral administration, the essential active ingredient may be combined with various sweetening or flavoring agents, coloring matter or dyes and, if so desired, emulsifying and/or suspending agents, together with such diluents as water, ethanol, propylene glycol, glycerin, and various combinations thereof.

Tablets may be uncoated or coated by known techniques to delay disintegration and adsorption in the gastrointestinal tract to thereby provide a sustained reaction over a longer period. For example, a time delay material such as glyceryl monostearate or glyceryl distearate may be employed. Formulations for oral use may also be presented as hard gelatin capsules wherein the active ingredients are mixed with an inert solid diluent, for example, lactose, mannitol, microcrystalline cellulose, calcium carbonate, calcium phosphate or kaolin, or as soft gelatin capsules wherein the active ingredients are present as such, or mixed with water or an oil medium, for example, peanut oil, liquid paraffin or olive oil. Tablets may be disintegrated for quick release of the active ingredients.

Surfactants that may be used to form the pharmaceutical compositions and dosage forms of the present invention include, but are not limited to, hydrophilic surfactants, lipophilic surfactants, and mixtures thereof. Specifically, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant will generally have an HLB value of at least 10, while suitable lipophilic surfactants will generally have an HLB value of or less than about 10. An empirical parameter commonly used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10.

However, the HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, examples of ionic surfactants include lecithins, lysolecithin, phospholipids, lysophospholipids and derivatives thereof carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

More preferred ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; and polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic non-ionic surfactants include, but are not limited to, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Examples of suitable lipophilic surfactants include: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In a preferred embodiment, the composition of the present invention may contain a solubilizer to ensure good solubilization or dissolution of the active ingredients, and to minimize precipitation of the active ingredients. This solubilizer may be particularly important in compositions for parenteral use, for example, injectable compositions. A solubilizer may also be added to increase the solubility of the hydrophilic drug and/or other agents, such as surfactants, or to maintain the composition as a stable or homogeneous solution or dispersion.

Examples of suitable solubilizers include, but are not limited to, alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Preferred solubilizers include, but are notlimited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer is limited to a biologically acceptable amount which may be readily determined by those skilled in the art. In some circumstances, it may be advantageous to include amounts of solubilizers far in excess of biologically acceptable amounts, for example to maximize the concentration of the hydrophilic drug, with excess solubilizer removed prior to providing the composition to a patient using conventional techniques, such as distillation or evaporation. Thus, if present, the solubilizer can be in a weight ratio of 10 wt %, 25 wt %, 50 wt %, 100 wt %, or up to about 200 wt %, based on the combined weight of the active ingredients and other excipients. If desired, very small amounts of solubilizer may also be used, such as 5%, 2%, 1% or less. Typically, the solubilizer will be present in an amount of about 1 wt % to about 100 wt %, more typically about 5 wt % to about 25 wt %.

The composition of the present invention may further contain one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavoring agents, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate may also be used. When the base is a salt, the cation can be any convenient and pharmaceutically acceptable cation, such as ammonium, alkali metals, alkaline earth metals, and the like. Preferred cations include sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

In some embodiments, the present invention provides an injectable pharmaceutical composition containing an agent for reducing or eliminating the side effects of component 1 and component 2 as active ingredient, particularly component 1. In some embodiment, the present invention provides an injectable pharmaceutical composition containing a combination of an agent for reducing or eliminating the side effects of component 1 and an injectable pharmaceutical excipient. The content of the agent in the composition is as described herein.

Forms that may be used to administer the novel composition of the present invention include aqueous or oily suspensions or emulsions, sesame oil, corn oil, cottonseed oil, peanut oil, elixirs, mannitol, dextrose, sterile aqueous solutions and similar pharmaceutical media.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. Proper fluidity can be maintained, for example, by the use of a coating, such as lecithin, by the maintenance of the required particle size in the case of dispersion and by the use of surfactants. Prevention of the action of microorganisms may be ensured by the inclusion of various antibacterial and antifungal agents, for example, paraben, chlorobutanol, phenol sorbic acid, and the like.

Sterile injectable solutions are prepared by incorporating the active ingredients in a required amount in an appropriate solvent with various other ingredients as enumerated above, as required, followed by filtered sterilization. Generally, dispersions are prepared by incorporating various sterile active ingredients into a sterile vehicle which contains a basic dispersion medium and the required other ingredients from those enumerated above. In the case of sterile powders for the preparation of sterile injectable solutions, the preferred methods of preparation are vacuum-drying and freeze-drying techniques which yield a powder of the active ingredients plus any additional desired ingredient from a previously sterile-filtered solution thereof.

Sterile injectable solutions are prepared by incorporating the required amount of antibiotic(s) in the appropriate solvent with other various ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, or dimethylsulfoxide (DMSO)-based solutions. In general, high-density carriers are capable of providing an area exposed to the active ingredients over a long period of time. In contrast, a solution formulation may provide more immediate exposure of the active ingredients to the chosen area.

The pharmaceutical compositions may also contain suitable solid or gel phase carriers or excipients, which are compounds that allow increased penetration of, or assist in the delivery of, therapeutic molecules across the stratum corneum permeability barrier of the skin. There are a number of penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another formulation for use in the methods of the present invention employs transdermal delivery devices (e.g., patches or minipumps). Such transdermal devices may be used to provide continuous or discontinuous infusion of the active ingredients in controlled amounts. Thus, in some embodiments the invention provides a transdermal device incorporating an agonist and/or an antagonist.

The construction and use of transdermal devices for the delivery of pharmaceutical agents is well known in the art. See, e.g., U.S. Pat. Nos. 5,023,252, 4,992,445 and 5,001,139. Such devices may be constructed for continuous, pulsatile, or on demand delivery of pharmaceutical agents.

Pharmaceutical compositions for inhalation: Compositions for inhalation or insufflation include solutions and suspensions in pharmaceutically acceptable aqueous or organic solvents, or mixtures thereof, and pharmaceutically acceptable powders. The liquid or solid compositions may contain suitable pharmaceutically acceptable excipients as described above. Preferably, the compositions are administered by the oral or nasal respiratory route for local or systemic effect. Preferably, compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension or powder compositions may be administered, preferably orally or nasally, from devices that deliver the formulation in an appropriate manner.

Other pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999)]; all of which are incorporated by reference herein in their entirety.

8. Dosage forms for combination therapy may be administered by any routes and methods, including, but not limited to, intravenous, intranasal, inhalation (e.g., intrapulmonary), sublingual, transdermal, subcutaneous and intracranial routes.

9. Neuropsychiatric disorders that may be treated with the combination therapy include PUD, LID and PTSD. In addition to PUD, LID and PTSD, indications include but not limited to: (1) Other substance-related disorders, including but not limited to tobacco use disorder, alcohol use disorder and cannabis use disorder; (2) behavioral addictive disorders, including but not limited to compulsive gambling and internet addiction; (3) other trauma and stressor-related disorders, including but not limited to reactive attachment disorder, acute stress disorder, and adjustment disorder; (4) anxiety disorders, including but not limited to generalized anxiety disorder, panic disorder, agoraphobia, substance/medication-induced anxiety disorder; (5) obsessive-compulsive disorders, including but not limited to obsessive-compulsive disorder, body dysmorphic disorder, hoarding disorder, trichotillomania, and excoriation disorder; and (6) feeding and eating disorders, including but not limited to anorexia nervosa, bulimia nervosa and binge-eating disorder.

10. A combination dosage form may be used together with other therapies or dosage forms to achieve additional or synergistic effects compared to the combination dosage form given alone. Examples of therapy or dosage forms that may be used combination therapy include, but not limited to behavioral therapies such as cognitive behavioral therapy, extinction therapy and exposure therapy, and drug therapies that use anti-epileptics, antipsychotics, antidepressants or ketamine.

11. To the extent many of symptoms and signs of these disorders are often observed in patients with other primary neuropsychiatric diagnoses, as comorbid disorders, secondary symptoms/signs, and/or as side effects of treatments of these disorders, the combination therapy may be used as a synergistic, additive, ameliorative and/or preventive adjunct treatment.

12. In one preferred combination dosage form, component 1 is methylphenidate or any immediate-release formulation of methylphenidate, and component 2 is any delayed, pulsatile-release formulation of ondansetron. Any combination/permutation of the doses of methylphenidate and ondansetron may be used. Preferably, the dose of methylphenidate in the dosage form is equivalent to 0.1 to 80 mg of methylphenidate hydrochloride, and the dose of ondansetron in the dosage form is equivalent to 0.1 to 32 mg of ondansetron hydrochloride. More preferably, the dose of methylphenidate in the dosage form is equivalent to 1 to 80 mg of methylphenidate hydrochloride, and the dose of ondansetron in the dosage form is equivalent to 0.1 to 16 mg of ondansetron hydrochloride. Even more preferably, the dose of methylphenidate in the dosage form is equivalent to 5 to 60 mg of methylphenidate hydrochloride, and the dose of ondansetron in the dosage form is equivalent to 4 to 16 mg of ondansetron hydrochloride. Any permutation of the fixed doses of methylphenidate and ondansetron within the preferred dose ranges may be embodied in single dosage forms.

13. If stereoisomers of the substance selected as component 1 exist, any stereoisomers may be used alone or in a combination thereof in optimized proportions. The use of esmirtazapine, the S(+) stereoisomer of the antidepressant mirtazapine (e.g., Remeron®), as the Component 2 in dosage forms for treatment of LID is an example of preferred use of one stereoisomer over the others.

13.1. Mirtazapine is a tetracyclic, piperazino-azepine compound (1,2,3,4,10,14b-hexahydro-2-methylpyrazino[2,1-a]pyrido[2,3-c]benzazepine; $C_{17}H_{19}N_3$; molecular weight: 265.36), and is a noradrenergic and specific serotonergic antidepressant. Commercially-available mirtazapine preparations (e.g., Remeron®) are marketed as a 50:50 racemic mixture of the S(+) and R(−) enantiomers.

13.2. Mirtazapine has high affinities to 5-HT2A and 5-HT2C receptors, as well as for 5-HT3, adrenergic α2 and histamine H1 receptors. Furthermore, although this drug has minimal affinity to 5-HT1A receptors, the drug may also potentiate 5-HT1A-dependent neurotransmission through the blockade of α2 adrenergic auto- and heteroreceptors and subsequent indirect increases in serotonin release. Since the drug is a 5-HT2 and 5-HT3 receptor antagonist, 5-HT1A—mediated serotonergic transmission is preferentially enhanced (functional 5-HT1A agonist).

13.3. In comparison with the R(−) enantiomer, esmirtazapine: (1) shows higher affinity for 5-HT2A and 5-HT2C (and α2 adrenergic) receptors; (2) may be absorbed faster (but not more extensively) by an "enantioselective" transport process in the gut wall; and (3) may accumulated more in the brain. These findings suggest that relatively lower oral doses of Component 2 could be effective in the combination therapy of LID. Furthermore, esmirtazapine has a half-life that is approximately 50% shorter than the R(−) enantiomer. Thus, esmirtazapine is expected to be associated with lower incidences of untoward side effects such as excessive daytime somnolence compared to racemic mirtazapine (e.g., Remeron®) or the R(−) enantiomer.

13.4. Esmirtazapine is predominantly metabolized by CYP2D6, which exhibits clinically-significant genetic polymorphism. Thus, its clearance is twice as low in poor metabolizers as compared to extensive metabolizers. Therefore, while any doses of esmirtazapine may be embodied in single combination therapy dosage forms, determination of the CYP2D6 phenotype in individual patients prior to the initiation of combination therapy may allow for a selection of pharmacogenetically-preferred esmirtazapine dose for individual patients ("individualized medicine").

MODE FOR INVENTION

Example 1: [MPh-IR+Ond-PR2]: Proof-of-Concept Phase IIA Safety/Efficacy Study

Ond-PR2 is a bead formulation prepared from ondansetron as the active pharmaceutical ingredient (API). MPh-IR is an immediate-release generic formulation of methylphenidate. [MPh-IR+Ond-PR2] is a single encapsulated dosage form consisting of MPh-IR and Ond-PR2 as Components 1 and 2, respectively. Following in vitro dissolution testing and PK and safety determinations in normal healthy volunteers (Phase 1 trial), we conducted a proof-of-concept, randomized, double-blind, placebo-controlled Phase 2A safety/efficacy clinical trial. A total of 48 patients residing in a residential program and meeting the DSM-4 criteria for primary psychostimulant abuse were screened, and 30 qualifying subjects were randomized into either [MPh-IR+Ond-PR2] or placebo treatment group.

Single capsules containing either [MPh-IR+Ond-PR2] or dextrose (placebo) were administered once a day for 14 days. Subjects also underwent single fMRI-based assessments 1-7 days before the first study dosing (pre-treatment) and again between Day 3 and 7 days after the last dosing (i.e., post-treatment assessment was performed after complete drug washout). Outcome measures for group comparisons were behavioral rating scales and blood-oxygenation-level-dependent (BOLD) functional imaging results under well-established resting-state, cue-reactivity and Go/noGO task paradigms. Twenty-eight subject completed the 2-week drug treatment and pre- and post-treatment fMRI assessments.

PK Analysis of [MPh-IR+Ond-PR2]

On Day 1 and Day 14, 24-four-hour blood PK samples were collected following single oral administrations of a [MPh-IR+Ond-PR2] capsule to: (1) estimate the PK parameters of the two Components (i.e., MPh-IR and Ond-PR2] by quantifying serum methylphenidate and ondansetron concentrations; and (2) determine whether or not any of these parameters change after single daily administrations for 14 days. Descriptive statistics for blood methylphenidate (MPh-IR) and ondansetron (Ond-PR2) concentrations at each time point were summarized as the mean, standard deviation and coefficient of variation. Estimation and statistical analyses of PK parameters were performed with SAS 9.3, and BABE Solution.

Table 1 presents the PK parameters of methylphenidate and ondansetron following a single oral administration of [MPh-IR+Ond-PR2] combination capsule on the first and last days of treatment (Days 1 and 14, respectively). No significant changes were observed in Cmax, Cmin, Tmax, t½, AUC (0-24), AUC (0-inf.), and Kel parameters for either methylphenidate or ondansetron between Day 1 and Day 14.

ate ($p<0.05$). Presented data are selected and represent examples.

Self-Reported Craving Scores after Exposure to Psychostimulant-Associated Visual Stimuli In the Phase 2A study on [MPh-IR+Ond-PR2], subjects provided craving rating scores during the cue-reactivity task in the neuroimaging scanner. We evaluated changes in craving ratings (post-treatment—pre-treatment) for each treatment group. ANCOVA (abstinence duration as the covariate) revealed that [MPh-IR+Ond-PR2] treatment for 14 days significantly reduced craving scores self-reported from inside the neuroimaging scanner (Table 2).

TABLE 2

|  | t, prob. > \|t\| | Mean Group Difference (post − pre) | 95% CI |
|---|---|---|---|
| Psychostimulant visual cue scale | 2.26, 0.033 | −1.63 | −3.12, −0.14 |
| SJS compulsive subscale | 2.28, 0.032 | −1.17 | −0.11, −2.22 |
| SJS negative feeling subscale | 2.07, 0.049 | −0.73 | −0.003, −1.45 |

In Table 2, prob.>|t| means the probability of obtaining the estimated value of mean group difference (e.g., −1.63 for psychostimulant cue reactivity), when actual difference is 0. For cocaine craving scores, the probability for the combination therapy group and the placebo group to have the same mean score (that is, no difference) is only 3.3%.

95% CI (95% Confidence Interval) means that there is a 95% confidence level that the true population mean difference between the combination therapy and the placebo groups falls between the low and high values (for example, −3.12 to −0.14 for compulsive cocaine scale). Confidence intervals which do not contain zero are declared significant difference between treatments with 95% confidence.

TABLE 1

| PK parameters | Day 1 | | Day 14 | |
|---|---|---|---|---|
|  | Methylphenidate | Ondansetron | Methylphenidate | Ondansetron |
| $C_{max}$, ng/ | 4 (2.6) | 11.2 (8.5) | 3.4 (2.8) | 12.6 (10.5) |
| $C_{min}$, ng/ | 0 | 2.7 (2.4) | 0 | 3.3 (2.7) |
| $T_{max}$, h | 1.9 (0.9) | 6.3 (2.0) | 1.7 (1.1) | 5.8 (0.9) |
| Half life($t_{1/2}$), h | 3.2 (0.6) | 6.9 (1.7) | 3.1 (0.4) | 7.2 (2.0) |
| AUC (0-24), h × ng/ | 21.5 (7.3) | 135.8 (94.4) | 21.5 (10.9) | 186.4 (118.5) |
| AUC (0-inf), h × ng/ | 21.6 (7.4) | 178.9 (127.6) | 23.4 (9.2) | 226.4 (157.2) |
| $K_{el}$, h − 1 | 0.2 (0.0) | 0.1 (0.0) | 0.2 (0.0) | 0.1 (0.0) |

WinNonlin non-compartmental PK analysis: Cmax, the maximum plasma concentration; Cmin, the minimum blood concentration before the next administration; Tmax, the time taken to reach the maximum plasma concentration; AUC (0-24), the area-under-curve of plasma concentration/time from 0 to 24 hours; AUC (0-inf), the area-under-curve of concentration/time presumed to be infinity; Kel, elimination rate constant (mean ± SD). The Tmax separations between the two Components of [MPh-IR + Ond-PR2] (methylphenidate and ondansetron) ranged 2-7 hrs. in individual study subjects, and did not change during the 14-day treatment (4.5 ± 1.2 vs. 4.4 ± 1.4 h on Day 1 and Day 14, respectively; mean ± SD)

Efficacy of [MPh-IR+Ond-PR2] in PUD Patients

All pre-treatment and post-treatment behavioral rating and fMRI data were first transformed into post-pre difference scores. The resulting [post-pre] scores for the placebo and [MPh-IR+Ond-PR2] groups were compared using one-way analyses of covariance (ANCOVA) with individual subjects' abstinence durations (3.0-12 months) as the covari- Shiffman-Jarvik Subscale Score The majority of PUD patients use tobacco products regardless whether they are also diagnosed with tobacco use disorder as a co-morbid disorder. The Shiffman-Jarvik Withdrawal Scale (SJWS) is one of psychological tests used to assess nicotine withdrawal symptoms (Shiffman and Jarvik, 1976). A short version of the SJWS (McClernon et al., 2005) was administered to PUD patients before and after [MPh- IR+Ond-PR2] or placebo treatment during the pre- and post-treatment neuroimaging sessions. ANCOVA (abstinence duration as the covariate) revealed that [MPh-IR+Ond-PR2] treatment for 14 days significantly reduced scores on SJS craving and negative affect subscales in patients diagnosed with PUD (Table 2).

Figure 3:
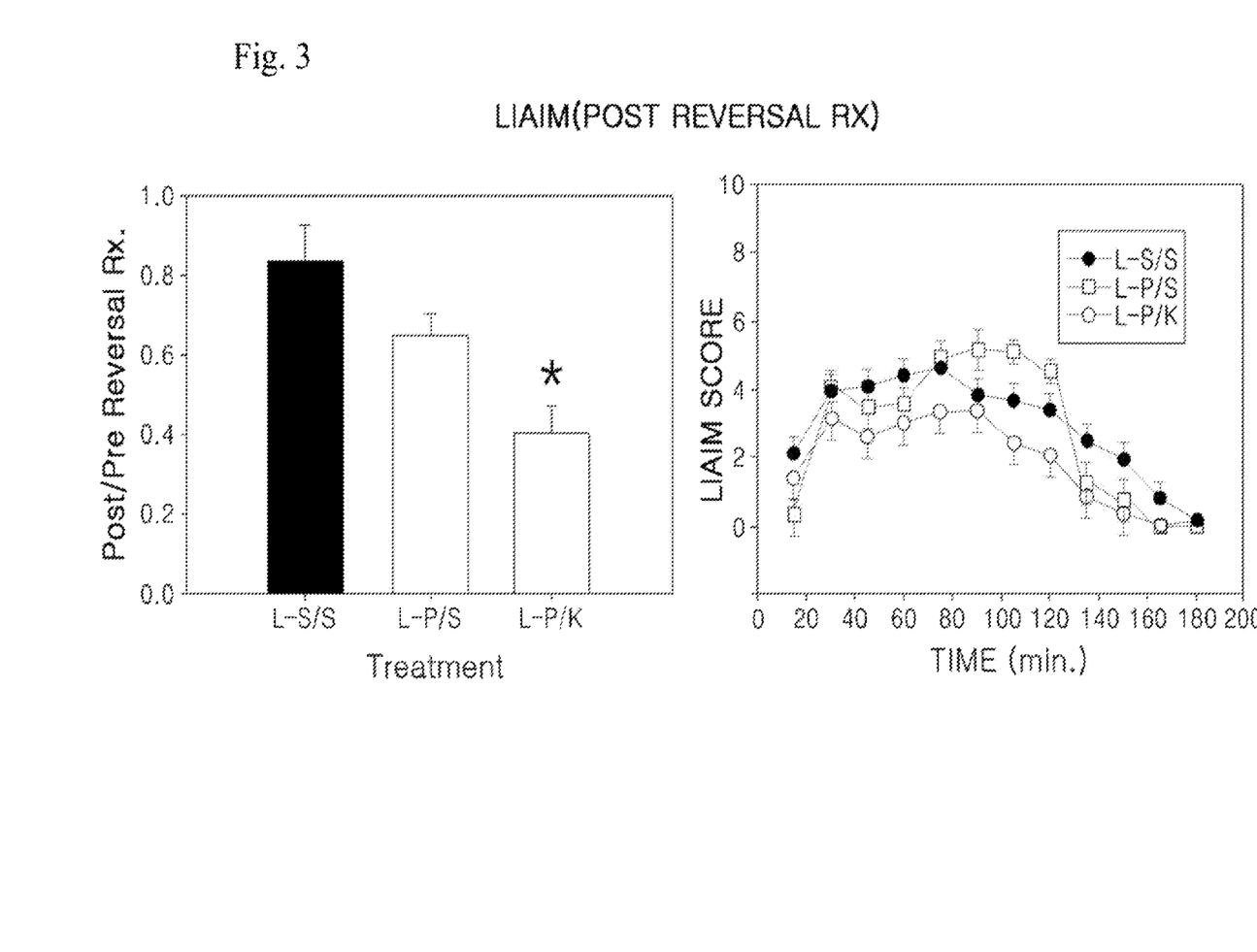
FIG. 3 shows that a combination of the DA agonist pergolide and the 5-HT2A/2C antagonist ketanserin significantly reduces levodopa-induced abnormal involuntary movement (LIAIM) in rat models of LID.

Example 2: Reversal of Levodopa-Induced Abnormal Involuntary Movement (LIAIM) by Treatment with Pergolide and Ketanserin In order to demonstrate that the agonist/antagonist combination therapy according to the present invention can effectively reverse LID and restore levodopa efficacy, an animal model study of LID was carried out using a combination of the DA agonist pergolide and the 5-HT2A/2C antagonist ketanserin. In this study, it was found that the combination therapy significantly reduced levodopa-induced abnormal involuntary movement (LIAIM) in the rat animal models of LID (FIG. 3).

Preparation of the animal models used in this experiment was performed as follows.

First, the dopaminergic neurotoxin 6-hydroxydopamine (6-OHDA) was injected into the right medial forebrain bundle of rats to induce unilateral lesions of the nigrostriatal DA pathway. Starting 3 weeks after 6-OHDA lesion, animals were treated twice daily with levodopa methyl ester (25 mg/kg, i.p., bid immediately preceded by 6.5 mg/kg, i.p. benserazide) for 3 weeks to establish LIAIM. Three hour LIAIM scores were quantified twice a week during the levodopa treatment using standard LIAIM rating scales.

Following LIAIM establishment, animals with combined limb, axial and orolingual LIAIM severity scores>25 were treated with one of the 3 treatment regimens for 2 weeks: (1) pergolide (0.1 mg/kg) followed 3.5 hours later by the 5-HT2A/2C antagonist ketanserin (1 mg/kg) [L_PK group]; (2) pergolide+saline 3.5 hours later [L_PS Group]; and (3) DMSO (1% in saline)+saline 3.5 hours later [L_SS]. All injections were given subcutaneously.

Two days after the last L_PK, L_PS or L-SS treatment, all animals were challenged with 25 mg/kg levodopa and their LIAIM scores were again quantified. Significant reversal treatment effects were found for the total LIAIM scores, expressed as the ratios between post- and pre-reversal treatment scores (F(2,23)=8.841, $p<0.001$, one-way ANOVA; FIG. 2, left panel); post-hoc Newman-Keul's test revealed that the combined pergolide/ketanserin treatment (L_P/K) significantly reduced LIAIM, compared to L_SS or L_P/S treatments ($p<0.05$). No differences were observed between the latter two groups. The right panel presents the full-time courses, which reveals that L-P/K exhibit reduced peak LIAIM scores as well as faster LIAIM offset.

INDUSTRIAL APPLICABILITY

The present invention may be used in the pharmaceutical industry and related industries, such as preparation of combination therapy compositions for treatment of neuropsychiatric disorders.

What is claimed is:

1. A method of treating a psychostimulant use disorder in a subject in need thereof, comprising:
    (a) identifying a patient meeting DSM-5 diagnostic criteria for psychostimulant use disorder;
    (b) administering a single dosage form to the patient, the single dosage form comprising:
    an immediate-release formulation of methylphenidate, or a pharmaceutically acceptable salt thereof; and
    a delayed and pulsatile release formulation of ondansetron, or a pharmaceutically acceptable salt thereof;
    wherein the immediate-release formulation of methylphenidate or a pharmaceutically acceptable salt thereof has an in vitro dissolution rate-profile of greater than or equal to about 90% in less than or equal to two hours, or greater than or equal to about 80% in less than or equal to one hour, under simulated gastric or intestinal dissolution test conditions, and the methylphenidate released from the single dosage form reaches a maximum plasma or serum concentration at a $Tmax_1$;
    wherein the delayed and pulsatile release formulation of ondansetron, or a pharmaceutically acceptable salt thereof; has an in vitro dissolution profile of less than or equal to 10% in greater than or equal to 3 hours, and greater than or equal to about 80% in less than or equal to 7 hours, under simulated gastric or intestinal dissolution test conditions, and the ondansetron released from the single dosage form reaches a maximum plasma or serum concentration at a $Tmax_2$; and
    wherein the difference between $Tmax_1$ and $Tmax_2$ ranges from about 2 to about 7 hours.

2. The method of claim 1, wherein the methylphenidate has a terminal elimination half-life of less than or equal to 5 hours and the ondansetron has a terminal elimination half-life of about 3 hours to 13 hours.

3. A method of treating a tobacco use disorder in a subject in need thereof, comprising:
    (a) identifying a patient meeting DSM-5 diagnostic criteria for tobacco use disorder;
    (b) administering a single dosage form to the patient, the single dosage form comprising:
    an immediate-release formulation of methylphenidate, or a pharmaceutically acceptable salt thereof; and
    a delayed and pulsatile release formulation of ondansetron, or a pharmaceutically acceptable salt thereof;
    wherein the immediate-release formulation of methylphenidate or a pharmaceutically acceptable salt thereof has an in vitro dissolution profile of greater than or equal to about 90% in less than or equal to two hours, or greater than or equal to about 80% in less than or equal to one hour, under simulated gastric or intestinal dissolution test conditions, and the methylphenidate released from the single dosage form reaches a maximum plasma or serum concentration at a $Tmax_1$;
    wherein the delayed and pulsatile release formulation of ondansetron or a pharmaceutically acceptable salt thereof has an in vitro dissolution profile of less than or equal to 10% in greater than or equal to 3 hours, and greater than or equal to about 80% in less than or equal to 7 hours, under simulated gastric or intestinal dissolution test conditions and the ondansetron released from the single dosage form reaches a maximum plasma or serum concentration at a $Tmax_2$; and
    wherein the difference between $Tmax_1$ and $Tmax_2$ ranges from about 2 to about 7 hours.

4. The method of claim 3, wherein the methylphenidate has a terminal elimination half-life of less than or equal to 5 hours and the ondansetron has a terminal elimination half-life of about 3 hours to 13 hours.

5. A method of treating an alcohol use disorder in a subject in need thereof, comprising:
    (a) identifying a patient meeting DSM-5 diagnostic criteria for alcohol use disorder;

(b) administering a single dosage form to the patient, the single dosage form comprising:

wherein the immediate-release formulation of methylphenidate or a pharmaceutically acceptable salt thereof, has an in vitro dissolution profile of greater than or equal to about 90% in less than or equal to two hours, or greater than or equal to about 80% in less than or equal to one hour, under simulated gastric or intestinal dissolution test conditions, and the methylphenidate released from the single dosage form reaches a maximum plasma or serum concentration at a $Tmax_1$; and wherein the delayed-pulsatile release formulation of ondansetron or a pharmaceutically acceptable salt thereof, having has an in vitro dissolution profile of less than or equal to 10% in greater than or equal to 3 hours, and greater than or equal to about 7080% in less than or equal to 7 hours, under simulated gastric or intestinal dissolution test conditions and the ondansetron released from the single dosage form reaches a maximum plasma or serum concentration at a $Tmax_2$; and wherein the difference between $Tmax_1$ and $Tmax_2$ ranges from about 2 to about 7 hours.

6. The method of claim 5, wherein the methylphenidate has a terminal elimination half-life of less than or equal to 5 hours and the ondansetron has a terminal elimination half-life of about 3 hours to 13 hours.

* * * * *

UNITED STATES PATENT AND TRADEMARK OFFICE
CERTIFICATE OF CORRECTION

PATENT NO. : 12,311,056 B2
APPLICATION NO. : 18/121626
DATED : May 27, 2025
INVENTOR(S) : Tong Hyon Lee It is certified that error appears in the above-identified patent and that said Letters Patent is hereby corrected as shown below:

In the Claims

Column 24, Line 7, delete "rate-".

Signed and Sealed this
Nineteenth Day of August, 2025

Coke Morgan Stewart
*Acting Director of the United States Patent and Trademark Office*